United States Patent [19]

Murch

[11] 3,943,196

[45] Mar. 9, 1976

[54] ALKOXY DERIVATIVES OF THE ADDUCT FROM PHOSPHORUS OXYCHLORIDE AND HEXAMETHYLPHOSPHORAMIDE

[75] Inventor: Robert M. Murch, Ashton, Md.

[73] Assignee: The United States of America as represented by the Secretary of the Navy, Washington, D.C.

[22] Filed: June 19, 1974

[21] Appl. No.: 480,919

[52] U.S. Cl............ 260/926; 260/45.7 P; 260/551 P
[51] Int. Cl.² ........................................... C07F 9/02
[58] Field of Search ............................ 260/926, 920

[56] References Cited
OTHER PUBLICATIONS

Kosulapoff, "Organophosphorus Compounds," J. Wiley & Sons, Inc., New York, (1950), p. 226.

*Primary Examiner*—Anton H. Sutto
*Attorney, Agent, or Firm*—R. S. Sciascia; A. L. Branning; T. McDonnell

[57] ABSTRACT

The adduct of phosphorous oxychloride and hexamethylphosphoramide and alkoxy derivatives thereof useful for enhancing the fire retardancy of polyesters and a method of enhancing the fire retardancy of general purpose polyester resins through the combination therewith of an alkoxy derivative of the adduct of phosphorous oxychloride and hexamethylphosphoramide.

3 Claims, No Drawings

3,943,196

ALKOXY DERIVATIVES OF THE ADDUCT FROM PHOSPHORUS OXYCHLORIDE AND HEXAMETHYLPHOSPHORAMIDE

BACKGROUND OF THE INVENTION

General purpose polyester resins can be used for most types of molding and laminating. By polyester is meant the polycondensation product of dicarboxylic acids with dihydroxy alcohols in contradistinction to materials known as alkyds. These polyester compounds may be modified by mono-carboxylic acids, monohydroxy alcohols and small amounts of polycarboxylic acids or polyhydroxy alcohols. Such compounds have a range of properties that may make it suitable for one purpose but unsuitable for another. For example, high viscosity resins are useful in vertical layup, where low viscosity resins, however, would be required when rapid penetration was desirable.

The wide range of properties possible with polyester resins leads to a variety of applications. They can be used as the primary polymer in fiber reinforced laminates and as the binder in composites containing a variety of inert fillers. Castings, potting compounds, cements, sealing and patching compounds, rigid and flexible coatings and adhesives can be based on polyester resins. As distinct from saturated polyesters, the resins contain olefins which produce the highly cross-linked structure generally known as a thermoset polymer.

While the uses of general purpose polyester resins continue to steadily grow, such resins suffer from the drawback that due to their high hydrogen and carbon content they continue to burn fairly readily once ignited. Since much concern has been generated by consumers to reduce the flammability of products such as flammable fabrics, manufacturers have had to find ways to reduce the flammability of polyesters and polyester resins.

The flammability of polyester resins can be reduced in several ways. These include chemical modification of one or more of the resin components, addition of organic fire retardants or addition of inorganic fillers and fire retardants.

A common chemical modification is replacing the diacid with a diacid containing halogen. Tetrachlorophthalic and tetrabromophthalic anhydrides are commonly used. One of the most widely used anhydrides is chlorendic anhydride, made by the Diels-Alder addition of hexachlorocyclopentadiene to maleic acid.

Other common polymer modifications include post bromination of the resin and the use of brominated diols. Halogenated styrene has been used and there are numerous known examples of the attachment of phosphorus-containing moieties to the diols, diacids or cross-linking olefins.

Two main types of organic compounds are commonly used as soluble, non-reactive additives. Halogen-containing aliphatic or aromatic compounds are commonly cited. Phosphorus compounds such as triethylphosphate are also well known in the art. Currently the combination of the two, i.e., tris-β-chloroethylphosphate or 2,3-dibromopropylphosphate have been widely used. In all of these cases the amount of additive is limited by possible plasticizing effects. Even small amounts of organometallics, examples being ferocene or ferocene derivatives have been recommended as desirable additives.

A number of inorganic additives are commonly added. Of course, glass fibers or cloth are used to increase the strength of the resin, but this may or may not help the flammability. The use of inert fillers such as calcium carbonate, magnesium oxide, etc. usually help the flammability characteristics in a minor way. The addition of hydrated salts and oxides, aluminatrihydrate being the most widely used, are effective by acting as a heat sink that slows down the energy transfer to the polymer. Antimony oxide is used, usually in conjunction with halogens, the latter may be incorporated as part of the resin or as a separate additive. Another commonly used inorganic additive is zinc borate.

SUMMARY OF THE INVENTION

It is therefore an object of the present invention to provide general purpose polyester resins having low flammability characteristics.

Another object of the invention is to provide additives which when added to general purpose polyester resins will enhance the fire retardancy of those resins.

Another object of the invention is to provide a method for enhancing the fire retardancy of polyester resins.

And another object of the invention is to provide fire retardant additives for general purpose polyester resins which are cheap and readily available.

Yet another object of the invention is to provide fire retardant additives for general purpose polyester resins which give minimum interference with the properties of the resins.

And yet another object of the invention is to provide a general purpose polyester resin having a low flammability without having a reduced outside durability.

These and other objects are achieved by reacting phosphorous oxychloride with hexamethylphosphoramide, then by reacting the adduct thereof with an alcohol, and by including the resulting alkoxy derivative with polyester resins.

DETAILED DESCRIPTION

In accordance with the novel aspects of the invention, general purpose polyester resins are rendered fire retardant by an additive. By "fire retardant" is meant that the resin is resistant to flame after the igniting flame has been removed. In other words the fire retardant polyester resins will not support combustion by itself. When in contact with an open flame, however, it may become charred.

Generally, polyesters are formed by the reaction of a dibasic acid with a polyhydric alcohol, such as, ethylene glycol. If either the acid or the alcohol is unsaturated, an unsaturated polyester is obtained that is capable of subsequent cross-linking either directly to similar unsaturated double bonds in adjacent polyester chains of the same structure or through an unsaturated double bond in a monomer such as styrene. An example of the latter is poly (propylene maleate/phthalate) in styrene which has long been used as a guide to compare with other more complex polyester resins. It is produced by reacting 2 moles of propylene glycol, 1 mole of phthalic anhydride, 1 mole of maleic anhydride, hydroquinone equal to 0.2% by volume of the final solution, and monomer styrene equaling 35% by volume of the final solution. In the examples hereinafter presented poly (propylene maleate/phthalate) in styrene was used to test the ability of the additive to render polyester resins fire retardant.

The fire retardancy enhancing additives of this invention are best produced by mixing at room temperature for at least about 10 minutes but preferably for 20 minutes in a mole ratio of 1:1 phosphorous oxychloride ($POCl_3$) with hexamethylphosphoramide ($Me_2N)_3PO$) in an amount of benzene at least sufficient to dissolve the reactants. This produces the adduct of $POCl_3$ and $(Me_2N)_3PO$ which has utility as a fire retardant itself, but due to an adverse side reaction when mixed with a polyester, this adduct is less important than its alkoxy derivative for polyester systems.

At the completion of the reaction which is evidenced by the reaction mixture becoming clear, the mixture is allowed to cool to 20° to 50° Centigrade below the reaction mixture's reflux temperature of approximately 80°C. The purpose of this step is to prevent the forthcoming adduct-alcohol reaction from becoming uncontrolled. Such a condition would be evidenced by a markedly turbulent reaction mixture. The adduct-alcohol reaction is carried out by mixing together the aforementioned reaction mixture with an alcohol in an alcohol-to-$POCl_3$ mole ratio of 3:1 and with pyridine in a pyridine-to-$POCl_3$ mole ratio of 3:1 for at least about 10 minutes. Also the reaction mixture may be heated to reflux temperature after the addition of the alcohol. Isolation of the resulting product is achieved by filtering the byproduct, pyridine hydrochloride and then by evaporating the solvent.

Alcohols found useful are methanol, ethanol, β-chloroethanol, 3,3,3-trichloropropanol, 2,3-dibromopropanol, 1,3-dichloro-2-propanol, and 2,2,2-trichloroethanol. It is expected that a good many other alcohols would yield similar results.

The fire retardancy of a general purpose polyesters is increased with the additives of the present invention by admixing one or more of them with a polyester in an amount from about 5 to about 20 weight percent of the total mixture. Inclusion of the additive is made after the polyester is prepared, but before it is cured.

As stated previously, polyester resins may be cross-linked either directly or through an unsaturated monomer. When cross-linked quite often a catalyst is used. Among the catalysts useful for such purposes are the peroxides. Some decompose at high temperatures, therefore, the choice of an appropriate catalyst depends on the intended molding or curing temperature. Benzoyl peroxide starts to decompose at 50°C and is therefore used for resins which are cured at high temperatures. Methylethyl ketone peroxide is used at lower temperatures especially with a cobalt accelerator such as cobalt naphthenate. Table I taken from *Polyesters and their applicatons*, Bjorksten Research Laboratories, Inc. Reinhold Publishing Corp., New York, 1956, p. 49 lists commonly used peroxide catalysts.

TABLE I

| Trade Name | Composition | Physical form | Peroxide assay % | Supplier* |
|---|---|---|---|---|
| — | Benzoyl peroxide | granules | 96 | 2 |
| — | Benzoyl peroxide | fine granules | 96 | 2 |
| — | Benzoyl peroxide purified | fine crystals | 96 | 2 |
| LUCIDOL | Benzoyl peroxide | fine crystals | 96 | 1 |
| LUPERCO ATC | Benzoyl peroxide compounded with tricresyl phosphate | thick paste | 50 | 1 |
| CADOX BTP | Benzoyl peroxide compounded with tricresyl phosphate | thick paste | 50 | 2 |
| LUPERCO CDB | 2,4-Dichlorobenzoyl peroxide compounded with dibutyl phthalate | thick paste | 50 | 1 |
| LUPERSOL DDM | Methylethyl ketone peroxide in dimethyl phthalate | liquid | 60 | 1 |
| CADON MDP | Methylethyl ketone peroxide in dimethyl phthalate | liquid | 60 | 2 |
| — | Cyclohexanone peroxide (mixed ketone peroxides) | granules | 96 | 1 |
| LUPERCO JDB | Cyclohexanone peroxide compounded with dibutyl phthalate | thick paste | 50 | 1 |
| — | Cumene hydroperoxide | liquid | 73 (as hydroperoxide) | 3 |

*Supplier:
(1) Lucidol Div., Wallace and Tiernan, Inc., Buffalo, N.Y.
(2) McKesson and Robbins, Inc., Chem. Div., N.Y. (distributors for Cadet Chem. Corp., Buffalo, N.Y.)
(3) Hercules Powder Co., Nav. Stores Dept., Wilmington, Del.

Other peroxide catalysts mentioned in the polyester patent literature are bis(para-bromobenzoyl) peroxide, bis(phthalyl) peroxide, bis(para-chlorobenzoyl) peroxide, bis(succinyl) peroxide, acetylbenzoyl peroxide, bis(chloroacetyl) peroxide, bis(acetyl) peroxide, tertiary-butyl perbenzoate, tertiary-butyl hydroperoxide, bis(dichlorobenzoyl) peroxide, oxonides such as di-isopropylene oxonide and di-isobutylene oxonide, peracetic acid, perbenzoic acid, benzoyl peracetate, and peroxy-carbonates such as ethyl peroxydicarbonate.

Accelerators other than cobalt naphthenate may be used as well. Among these are the vanadium accelerators and dimethyl-p-toluidine. Other catalysts such as dimethylaniline may be used as well. When using these accelerators and catalysts to promote cross-linking the polyester resin, it may be beneficial to heat the resin. The temperature at which to heat the resin is dependent upon the curing system being employed and is well within the skill of the art.

In order to more fully illustrate the invention the following examples are presented. The purpose of the examples is to illustrate the fire retardancy characteristics obtained by adding an alkoxy derivative of this invention to a general purpose polyester resin that is often used to make comparisons with other complex polyester resins. Therefore, the use herein of the general purpose polyester resin is meant to be illustrative and not a limitation as to the scope of the invention.

EXAMPLE 1

Phosphorous oxychloride, 46 g., was dissolved in 200 ml of benzene and then hexamethylphosphoramide, 53.5 g., was added slowly during a 20-minute period. The temperature of the reaction mixture rose from 25°C to 60°C during this addition. After cooling the mixture to 35°C, 2,2,2-trichloroethanol, 44.9 g., was added slowly and the reaction mixture was heated to the reflux temperature, 80°C. After 14 hours at this temperature the mixture was cooled, the solvent was removed by distillation and then additional volatiles removed by heating to 120°C at 0.3 mn Hg. The product weighed 70 g. for a yield of 52 percent. The product was a brown semi-solid.

EXAMPLE 2

Phosphorous oxychloride, 15.35 g., and hexamethyl phosphoramide 17.9 g. were combined in 150 ml of benzene in the same manner as in Example 1 and the temperature of the reaction rose to 35°C. After adding 4.6 g. of ethanol, the solution was heated to reflux and held at this temperature (80°C) for two hours. The product isolated by distilling solvent and volatiles weighed 27.0 g. for a yield of 79 percent.

EXAMPLE 3

Phosphorous oxychloride 15.3 g. and hexamethyl phosphoramide 17.9 were combined as in Example 1 in 150 ml of benzene. The exothermic reaction raised the temperature 12°C to 37°C. After cooling to 35°C, 12.9 g. of 1,3-dichloro-2-propanol, was added and the mixture was held at reflux, 70°C, for seven hours. The product was isolated by distilling the solvent and volatile materials up to a temperature of 100°C at 0.1 mm Hg. The product was viscous yellow liquid.

EXAMPLE 4

Phosphorous oxychloride, 15.35 g., and hexamethyl phosphoramide, 17.9 g., were combined in 150 ml of benzene and the temperature rose 13°C. Then 2,3-dibromopropanol, 21.8 g., was added and the mixture was heated at 80°C for 2 hours. After removing the solvent and volatile material by distilling to 120°C at 0.1 mm Hg the product was a brown viscous liquid weighing 21.9 g.

EXAMPLE 5

The product from Example 1 was added at the 10% level, i.e., 90 parts of resin, 10 parts of additive, to a general purpose polyester resin and the cure was effected with a cobalt accelerator and a methyl ethyl ketone peroxide and a curing period of 4 hours at 70°C.

The resin had a Barcol hardness of 42 and an oxygen index of 0.244. This same resin without the additive would have an oxygen index of .18.

EXAMPLE 6

A general purpose polyester resin containing 10 percent of the additive described in Example 2 was cured as described in Example 5. The resin had a Barcol hardness of 40 and an oxygen index of .248.

EXAMPLE 7

The same procedure with the additive from Example 3 gave a resin with a Barcol hardness of 40 and any oxygen index of 0.252.

EXAMPLE 8

The same procedure with the additive from Example 4 gave a resin with an oxygen index of 0.250 and a Barcol hardness of 40.

Example 1 illustrates the manner in which the adduct of phosphorous oxychloride and hexamethyl phosphoramide is produced, and illustrates the production of an alkoxy derivative encompassed by this invention. Examples 2–4 illustrate the production of alkoxy derivatives of this invention by reacting the adduct of Example 1 with three different alcohols. Examples 5–8 are illustrative of the use of alkoxy derivatives used as fire retardant additives to the polyester resins.

In the Examples the oxygen index was obtained by using the method disclosed under ASTMD2863-70. By "oxygen index" is meant the minimum oxygen concentration, expressed in volume percent, in a mixture of oxygen and nitrogen that will just support combustion of a material under the conditions of the method. Accordingly, a material having a high oxygen index requires more oxygen to support combustion, and is therefore more fire retardant then are having a low oxygen index. In each of the Examples the additive markedly enhanced the fire retardation capabilities of the polyester resin.

The polyester resin used in the Examples has an oxygen index of 0.18. It is apparent that the use of the additive of the invention significantly increases the fire retardancy of the resin.

Obviously many modificatons and variations of the present invention are possible in light of the above teachings. It is therefore to be understood that within the scope of the appended claims the invention may be practiced otherwise than as specifically described.

What is claimed and desired to be secured by Letters Patent of the United States is:

1. A compound having the formula: $(RO)_3P(O)\cdot(Me_2N)_3PO$, wherein R = $ClCH_2CH_2$, $Cl_3CCH_2$, $Cl_3CCH_2CH_2(ClCH_2)_2CH$, $CH_2BrCHBrCH_2$, $C_2H_5$ and $CH_3$.

2. The compound of claim 1 wherein R = $CH_2$ and $C_2H_5$.

3. The compound of claim 1 wherein R = $(ClCH_2)_2CH$, $Cl_3CCH_2CH_2$, and $CH_2BrCHBrCH_2$.

* * * * *